US011872000B2

(12) United States Patent
Kostrzewski

(10) Patent No.: US 11,872,000 B2
(45) Date of Patent: *Jan. 16, 2024

(54) ROBOTIC SURGICAL SYSTEMS AND METHODS

(71) Applicant: KB Medical SA, Audubon, PA (US)

(72) Inventor: Szymon Kostrzewski, Lausanne (CH)

(73) Assignee: Globus Medical, Inc, Audubon, PA (US)

( * ) Notice: Subject to any disclaimer, the term of this patent is extended or adjusted under 35 U.S.C. 154(b) by 462 days.

This patent is subject to a terminal disclaimer.

(21) Appl. No.: 16/888,917

(22) Filed: Jun. 1, 2020

(65) Prior Publication Data
US 2021/0038326 A1 Feb. 11, 2021

Related U.S. Application Data

(63) Continuation of application No. 15/253,206, filed on Aug. 31, 2016, now Pat. No. 10,687,905.
(Continued)

(51) Int. Cl.
*A61B 34/30* (2016.01)
*A61B 17/17* (2006.01)
(Continued)

(52) U.S. Cl.
CPC .............. *A61B 34/30* (2016.02); *A61B 5/24* (2021.01); *A61B 17/1757* (2013.01); *A61B 34/20* (2016.02); *A61B 34/70* (2016.02); *A61B 90/03* (2016.02); *A61B 90/11* (2016.02); *B25J 19/06* (2013.01); *G16H 20/40* (2018.01); *G16H 40/63* (2018.01); *A61B 5/4893* (2013.01);
(Continued)

(58) Field of Classification Search
CPC .......................................... A61B 34/30–34/77
See application file for complete search history.

(56) References Cited

U.S. PATENT DOCUMENTS

| 4,150,293 A | 4/1979 | Franke |
| 5,246,010 A | 9/1993 | Gazzara et al. |

(Continued)

FOREIGN PATENT DOCUMENTS

| JP | 201532227 A | 10/2010 | |
| WO | WO-2013192598 A1 * | 12/2013 | ............. A61B 10/02 |

OTHER PUBLICATIONS

US 8,231,638 B2, 07/2012, Swarup et al. (withdrawn)

*Primary Examiner* — Zade Coley

(57) ABSTRACT

The disclosed technology relates to robotic surgical systems for improving surgical procedures. In certain embodiments, the disclosed technology relates to robotic surgical systems for use in osteotomy procedures in which bone is cut to shorten, lengthen, or change alignment of a bone structure. The osteotome, an instrument for removing parts of the vertebra, is guided by the surgical instrument guide which is held by the robot. In certain embodiments, the robot moves only in the "locked" plane (one of the two which create the wedge—i.e., the portion of the bone resected during the osteotomy). In certain embodiments, the robot shall prevent the osteotome (or other surgical instrument) from getting too deep/beyond the tip of the wedge. In certain embodiments, the robotic surgical system is integrated with neuromonitoring to prevent damage to the nervous system.

19 Claims, 11 Drawing Sheets

Related U.S. Application Data

(60) Provisional application No. 62/212,551, filed on Aug. 31, 2015.

(51) Int. Cl.
    *A61B 90/00*         (2016.01)
    *A61B 34/20*         (2016.01)
    *B25J 19/06*         (2006.01)
    *A61B 90/11*         (2016.01)
    *A61B 34/00*         (2016.01)
    *G16H 20/40*        (2018.01)
    *G16H 40/63*        (2018.01)
    *A61B 5/24*          (2021.01)
    *A61B 17/16*         (2006.01)
    *A61B 17/00*         (2006.01)
    *A61B 18/00*         (2006.01)
    *A61B 5/00*          (2006.01)
    *A61B 34/10*         (2016.01)
    *A61B 34/32*         (2016.01)

(52) U.S. Cl.
    CPC ........... *A61B 17/1671* (2013.01); *A61B 34/25* (2016.02); *A61B 34/32* (2016.02); *A61B 2017/00039* (2013.01); *A61B 2018/00839* (2013.01); *A61B 2034/107* (2016.02); *A61B 2034/2055* (2016.02); *A61B 2034/2059* (2016.02); *A61B 2034/2068* (2016.02); *A61B 2090/062* (2016.02); *A61B 2090/064* (2016.02); *A61B 2090/066* (2016.02); *A61B 2090/3937* (2016.02)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,520,692 A * | 5/1996 | Ferrante ............ A61B 17/1677 606/88 |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |

(56) References Cited

U.S. PATENT DOCUMENTS

| | | |
|---|---|---|
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,569,058 B2 * | 8/2009 | Zwirnmann ....... A61B 17/1655 606/80 |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Wlliliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |

(56) References Cited

U.S. PATENT DOCUMENTS

| | | |
|---|---|---|
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 * | 10/2013 | Greer .................. B25J 9/1666 901/41 |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |

(56) References Cited

U.S. PATENT DOCUMENTS

| | | |
|---|---|---|
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0068187 A1* | 4/2004 | Krause ............... A61B 17/151 |
| | | 600/443 |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0016068 A1 | 1/2007 | Gunwald |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0183190 A1* | 7/2008 | Adcox ............... G16H 30/40 |
| | | 606/130 |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0088848 A1* | 4/2009 | Martz ............... A61B 17/1604 |
| | | 606/86 R |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |

(56) References Cited

U.S. PATENT DOCUMENTS

| | | |
|---|---|---|
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1* | 5/2014 | Kostrzewski ...... A61B 17/1703 901/3 |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1* | 7/2015 | Kostrzewski ...... A61B 17/3417 606/130 |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

\* cited by examiner

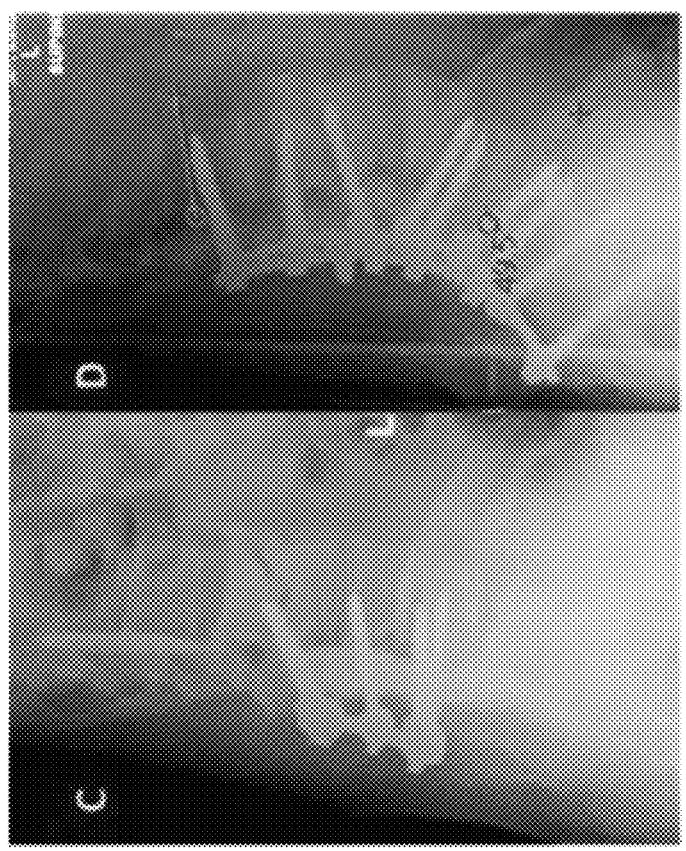
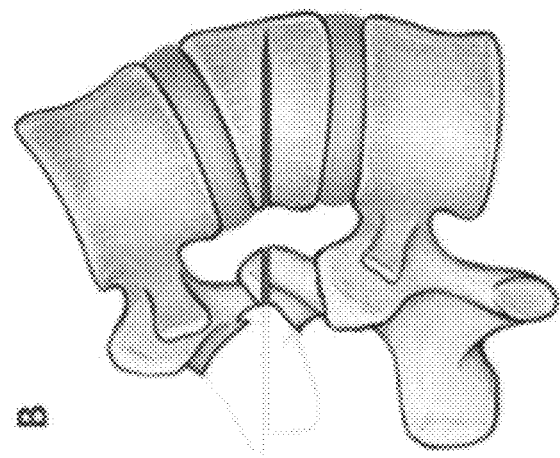
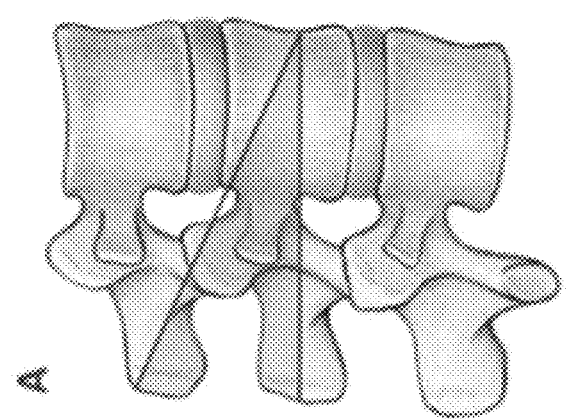
FIG. 2A  FIG. 2B  FIG. 2C  FIG. 2D

10mm STRAIGHT OSTEOTOME

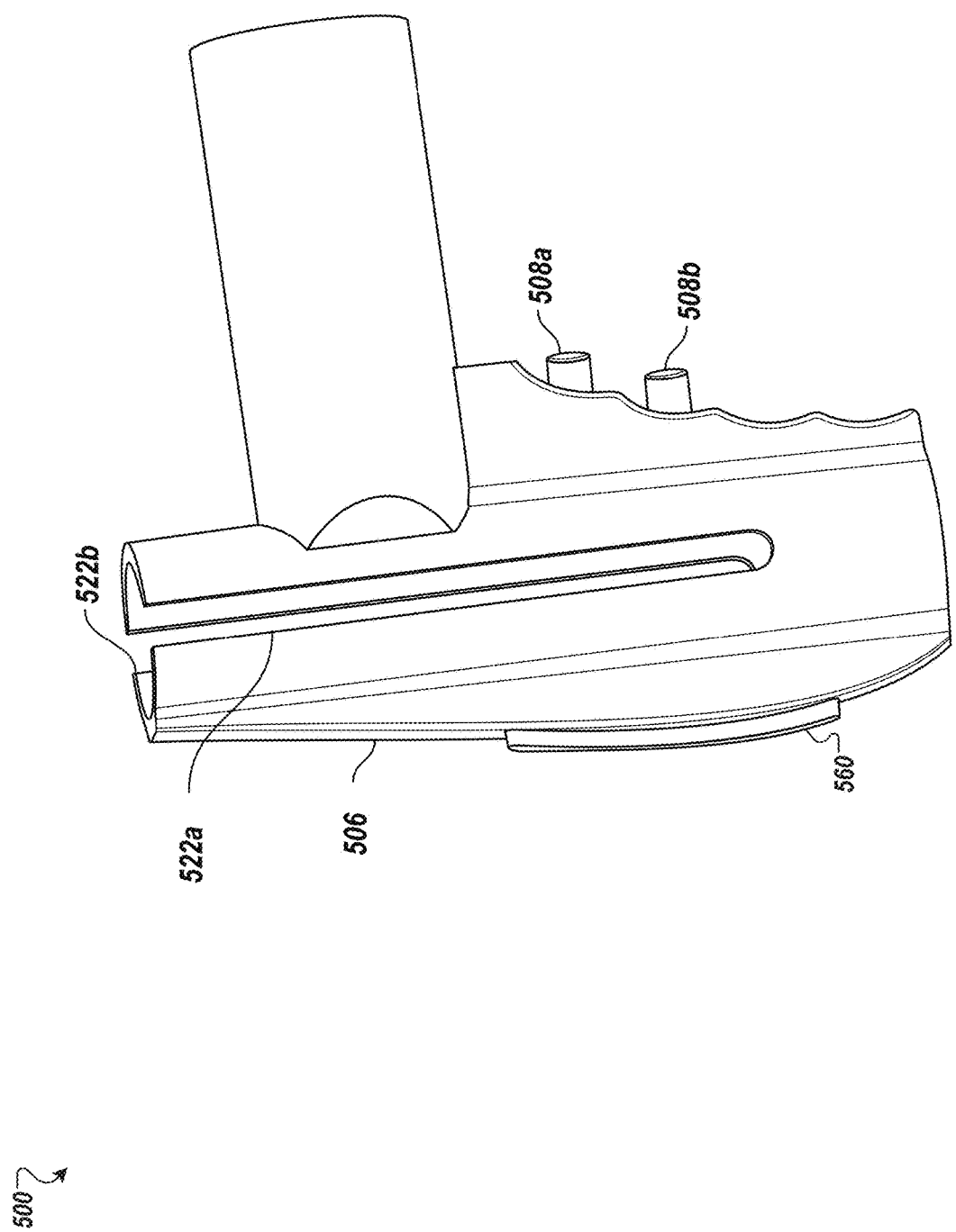

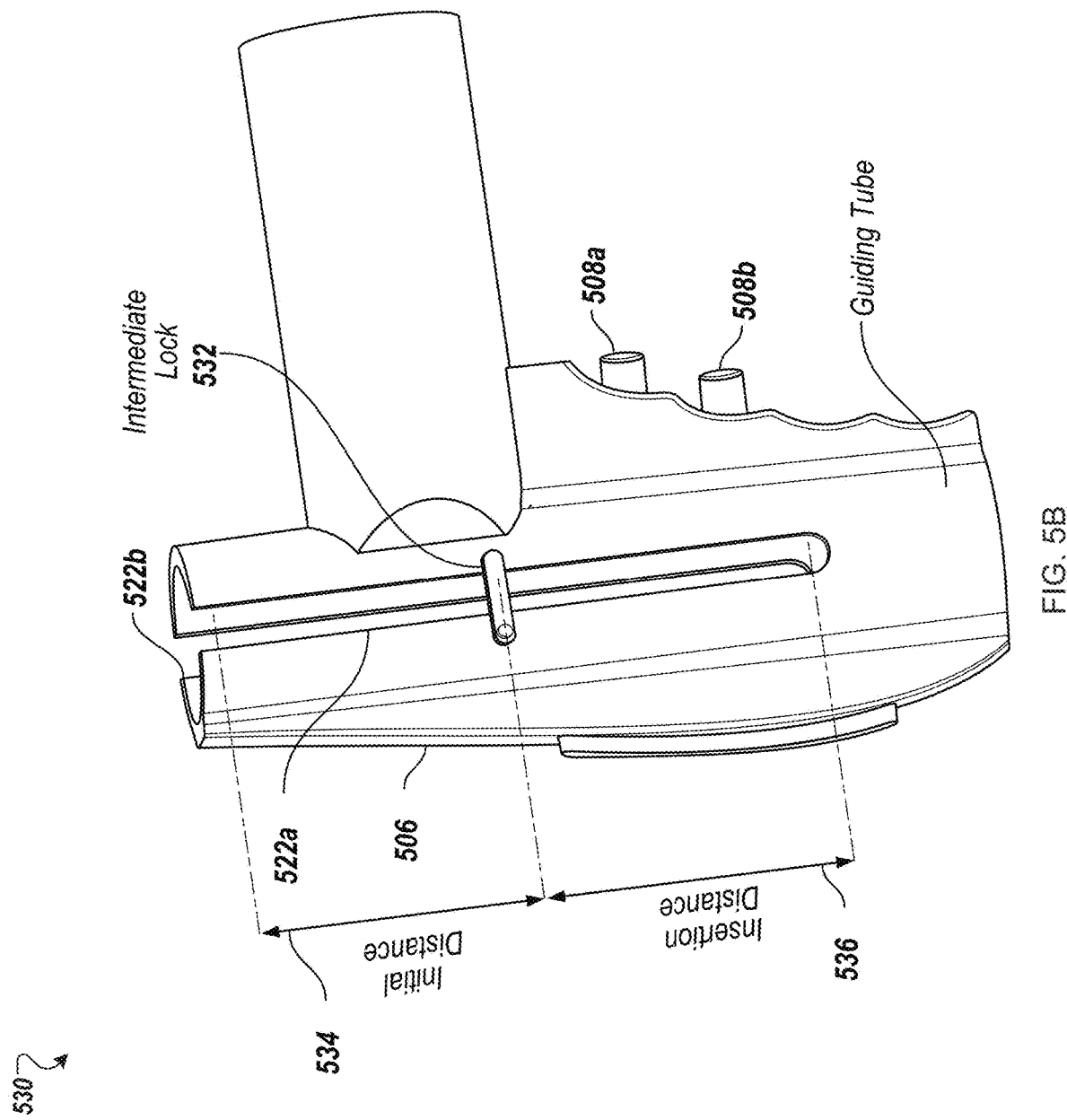

ROBOTIC SURGICAL SYSTEMS AND METHODS

RELATED APPLICATIONS

This application is a continuation of U.S. patent application Ser. No. 15/253,206, filed Aug. 31, 2016, which claims priority to U.S. Provisional Patent Application No. 62/212,551, filed Aug. 31, 2015, entitled "ROBOTIC SURGICAL SYSTEMS AND METHODS FOR SPINAL AND OTHER SURGERIES," the entire contents of which are hereby incorporated by reference.

BACKGROUND OF THE INVENTION

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeons field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Certain surgical procedures, such as neurosurgery, orthopedic surgery, and spinal surgery require precise movement of surgical instruments and placement of devices. For example, spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

In some procedures, such as osteotomy, a portion of the vertebra is removed (e.g., a wedge is created) such that the alignment of the spine can be changed. However, correcting the shape of the spine manually is difficult, prone to error, and cumbersome. For example, FIGS. 2A through 2D illustrate the principles of osteotomy, which is to correct the shape of the spine. A part of the vertebra is removed in order to obtain the right curvature of the spine. After part of the vertebra is removed, the vertebra(e) is fixed with the screws as shown in FIG. 2D to prevent spinal instability. An example osteotomy instrument is shown in FIG. 3. A surgeon manipulates this instrument, sometimes by hitting it with a hammer, to remove part of the vertebra(e). Similar procedures can be performed on other portions of a patient's skeletal structure.

Inaccurate or incorrect surgical procedures such as osteotomies, are frequent and typically the result of inadequacy of instruments and the difficulty of accurately removing portions of the bone with manual tools. Thus, there is a need for a robotic surgical system to assist with surgical procedures.

SUMMARY OF THE INVENTION

The disclosed technology relates to robotic surgical systems for improving surgical procedures. In certain embodiments, the disclosed technology relates to robotic surgical systems for use in osteotomy procedures in which bone is cut to shorten, lengthen, or change alignment of a bone structure. The disclosed technology can be used for many surgical procedures including, but not limited to, spinal surgery; neurosurgery (surgery performed on the nervous system), such as brain surgery; and orthopedic surgery, such as hip, knee, leg, or knee surgery.

The instrument, such as an osteotome for removing parts of bone, is guided by the surgical instrument guide which is held by the robot. In certain embodiments, the robot moves only in the "locked" plane (one of the two which create the wedge—i.e., the portion of the bone resected during the osteotomy). The guide allows for translational movement of the instrument, such as an osteotome, which is necessary to cut the bone (e.g., vertebra). A surgeon can, for example, use a hammer or advance the instrument only using his hand. In certain embodiments, a navigation marker measures the position of the instrument which is necessary for the system to determine the locked planes (e.g., the planes along which the cuts are made to form the wedge). In other embodiments, the marker is on the robot and robot's actual position (measured by robot's encoders and calculated using robot model) is used to determine the position of the instrument in space.

In certain embodiments, the robot shall prevent the instrument (or other surgical instrument) from getting too deep/ beyond the tip of the wedge. This can be achieved be having a notch at the correct distance above the patient thereby preventing the instrument from getting deeper than the notch end.

In certain embodiments, the robotic surgical system is integrated with neuromonitoring to prevent damage to the nervous system. For example, the electrical potential applied to the patient via the surgical instrument can be measured to ensure that the amount remains below an acceptable level. This can be measured by a neuromonitor (e.g., such as a neuromonitoring system with a sensor cable). When a threshold level is reached/detected or a nerve has been touched, a signal is sent to the appropriate system to stop insertion of the surgical instrument and/or move the surgical instrument away such that the depth of penetration is less.

In one aspect, the disclosed technology includes a robotic surgical system for use in a surgical procedure performed on a patient, the system including: a robotic arm including an end-effector; an actuator for controlled movement of the robotic arm and positioning of the end effector, thereby controlling the trajectory and/or insertion depth of a surgical instrument in a guide affixed to the end effector; a neuromonitoring module for implementing real-time neuromonitoring during a surgical procedure; and a processor and a memory storing instructions thereon, wherein the instructions, when executed, cause the processor to: receive, by the neuromonitoring module, a trigger based on a neurological response of a portion of a nerve structure of the patient that is measured by a neuromonitoring system; and prevent, by the neuromonitoring module, deeper insertion into the patient of a surgical instrument guided by the robotic surgical system upon receipt of the trigger.

In certain embodiments, the system includes preventing deeper insertion into the patient of a surgical instrument guided by the robotic surgical system upon receipt of the trigger including moving, by the robotic surgical system, a position of the end-effector away from the patient (e.g., along an axis).

In certain embodiments, the system includes a surgical instrument guide arranged to pass a neuromonitoring cable therethrough.

In certain embodiments, the surgical instrument guide is integrated with the neuromonitoring system such that a neuromonitoring cable can pass through a sterile zone.

In certain embodiments, the neuromonitoring system which is separate from the robotic surgical system.

In certain embodiments, the neuromonitoring system includes a cable that extends through a surgical instrument guide connected to the end-effector.

In certain embodiments, the surgical instrument guide includes a user interface thereon.

In certain embodiments, the user interface includes one or more buttons thereon.

In certain embodiments, the surgical instrument guide includes a block and/or notch (e.g., at a correct distance above the patient) for preventing further insertion of the surgical instrument.

In certain embodiments, the system includes a navigation module for maintaining the position of the end-effector upon detection, by a navigation system, of movement of a navigation marker.

In certain embodiments, the system includes a user interface on a robotic arm of the robotic surgical system.

In certain embodiments, the user interface includes a touch screen.

In certain embodiments, the instructions, when executed by the processor, cause the processor to: provide for display on the user interface a list of one or more trajectories for selection by a user.

In certain embodiments, the instructions, when executed by the processor, cause the processor to: limit movement of the end effector such that movement of the surgical instrument is limited to a locked plane (e.g., wherein the locked plane is long which one of the cuts to create a wedge in the vertebra(e) is made).

In certain embodiments, the instructions, when executed by the processor, cause the processor to: limit movement of the end effector such that movement of the surgical instrument is limited to translational movement (e.g., which is necessary to cut the vertebrae).

In certain embodiments, the instructions, when executed by the processor, cause the processor to: determine the position of the surgical instrument (e.g., osteotome).

In certain embodiments, the position of the surgical instrument is determined (e.g., for depth/insertion monitoring; e.g., to determine locked planes for the surgical instrument) by a navigation system based at least in part on the position of a marker on the osteotome.

In certain embodiments, the position of the surgical instrument is determined by a navigation system based at least in part on the position of a marker on the robotic surgical system and the robotic arms actual position (e.g., as measured by the robotic surgical systems encoders and calculated using the robotic surgical systems movement model).

In certain embodiments, the end effector is a force and/or torque control end-effector.

In certain embodiments, the end effector is configured to hold a first surgical tool.

In certain embodiments, the end-effector includes a tool holder attached to the robotic arm via a force sensor, wherein the tool holder is sized and shaped to hold a first surgical tool.

In certain embodiments, the system includes a manipulator configured to allow robotically-assisted or unassisted positioning and/or movement of the end-effector by a user with at least four degrees of freedom.

In certain embodiments, the system includes a handle extending from the end effector that may be grasp by a hand of a user to move and/or position the end effector.

In certain embodiments, the system includes a force sensor located between the robotic arm and the tool holder for measuring forces and/or torques applied by a user to the first surgical tool held by the tool holder.

In certain embodiments, the system includes a sensor that detects the presence of the hand of the user on the handle.

In certain embodiments, the robotic surgical system is configured to permit a surgeon to manually move the end-effector to a position for an operation.

In certain embodiments, the surgery is spinal surgery, neurosurgery, or orthopedic surgery.

In certain embodiments, the end-effector is configured to releasably hold the first surgical tool, allowing the first surgical tool to be removed and replaced with a second surgical tool.

In certain embodiments, the manipulator is configured to allow robotically assisted or unassisted positioning and/or movement of the end-effector by a user with at least six degrees of freedom, wherein the six degrees of freedom are three degrees of translations and three degrees of rotations.

In certain embodiments, the patient position is a position of one or more markers placed in spatial relation to one or more vertebrae.

In certain embodiments, controlling the actuator to move the end-effector includes controlling the actuator to move the end-effector in a direction corresponding to a direction of application of the force and/or torque.

In certain embodiments, the end-effector is configured to move at a predetermined measured pace upon application and detection of user force and/or torque applied to the end-effector in excess of the predetermined minimum force and/or torque and the predetermined measured pace is a steady, slow velocity.

In certain embodiments, the system includes the neuromonitoring system for providing depth control and/or protection.

In certain embodiments, the surgical instrument is an osteotome.

In another aspect, the disclosed technology includes a method of controlling the position of an end-effector of a robotic surgical system, the method including: receiving, by a neuromonitoring module of the robotic surgical system, a trigger from a neuromonitoring system, wherein the robotic surgical system includes: a robotic arm including the end-effector, an actuator for controlled movement of the robotic arm and positioning of the end effector, thereby controlling the trajectory and/or insertion depth of a surgical instrument in a guide affixed to the end effector, and the neuromonitoring module for implementing real-time neuromonitoring during a surgical procedure; and controlling, by a processor of a computing device in the robotic surgical system, a position of an end-effector of the robotic surgical system to prevent deeper insertion into a patient of a surgical instrument guided by the robotic surgical system upon receipt of the trigger.

In certain embodiments, preventing deeper insertion into the patient of a surgical instrument guided by the robotic surgical system upon receipt of the trigger including moving, by the robotic surgical system, a position of the end-effector away from the patient (e.g., along an axis).

In certain embodiments, the robotic surgical system includes a surgical instrument guide arranged to pass a neuromonitoring cable therethrough.

In certain embodiments, the surgical instrument guide is integrated with the neuromonitoring system such that a neuromonitoring cable can pass through a sterile zone.

In certain embodiments, the robotic surgical system includes the neuromonitoring system is separate from the robotic surgical system.

In certain embodiments, the neuromonitoring system includes a cable that extends through a surgical instrument guide connected to the end-effector.

In certain embodiments, the surgical instrument guide includes a user interface thereon.

In certain embodiments, the user interface includes one or more buttons thereon.

In certain embodiments, the surgical instrument guide includes a block and/or notch (e.g., at a correct distance above the patient) for preventing further insertion of the surgical instrument.

In certain embodiments, the method includes receiving, by a navigation module in the robotic surgical system, a navigation signal indicating movement of a navigation marker; and moving, by the robotic surgical system, a position of the end-effector based on the navigation signal.

In certain embodiments, the robotic surgical system includes a user interface on a robotic arm of the robotic surgical system.

In certain embodiments, the user interface includes a touch screen.

In certain embodiments, the instructions, when executed by the processor, cause the processor to: provide for display on the user interface a list of one or more trajectories for selection by a user.

In certain embodiments, the instructions, when executed by the processor, cause the processor to: limit movement of the end effector such that movement of the surgical instrument is limited to a locked plane (e.g., wherein the locked plane is long which one of the cuts to create a wedge in the vertebra(e) is made).

In certain embodiments, the instructions, when executed by the processor, cause the processor to: limit movement of the end effector such that movement of the surgical instrument is limited to translational movement (e.g., which is necessary to cut the vertebrae).

In certain embodiments, the instructions, when executed by the processor, cause the processor to: determine the position of the surgical instrument (e.g., osteotome).

In certain embodiments, the position of the surgical instrument is determined (e.g., for depth/insertion monitoring; e.g., to determine locked planes for the surgical instrument) by a navigation system based at least in part on the position of a marker on the osteotome.

In certain embodiments, the position of the surgical instrument is determined by a navigation system based at least in part on the position of a marker on the robotic surgical system and the robotic arms actual position (e.g., as measured by the robotic surgical systems encoders and calculated using the robotic surgical systems movement model).

In certain embodiments, the end effector is a force and/or torque control end-effector.

In certain embodiments, the end effector is configured to hold a first surgical tool.

In certain embodiments, the end-effector includes a tool holder attached to the robotic arm via a force sensor, wherein the tool holder is sized and shaped to hold a first surgical tool.

In certain embodiments, the robotic surgical system includes a manipulator configured to allow robotically-assisted or unassisted positioning and/or movement of the end-effector by a user with at least four degrees of freedom.

In certain embodiments, the robotic surgical system includes a handle extending from the end effector that may be grasp by a hand of a user to move and/or position the end effector.

In certain embodiments, the robotic surgical system includes a force sensor located between the robotic arm and the tool holder for measuring forces and/or torques applied by a user to the first surgical tool held by the tool holder.

In certain embodiments, the robotic surgical system includes a sensor that detects the presence of the hand of the user on the handle.

In certain embodiments, the robotic surgical system is configured to permit a surgeon to manually move the end-effector to a position for an operation.

In certain embodiments, the surgery is spinal surgery.

In certain embodiments, the end-effector is configured to releasably hold the first surgical tool, allowing the first surgical tool to be removed and replaced with a second surgical tool.

In certain embodiments, the manipulator is configured to allow robotically assisted or unassisted positioning and/or movement of the end-effector by a user with at least six degrees of freedom, wherein the six degrees of freedom are three degrees of translations and three degrees of rotations.

In certain embodiments, the patient position is a position of one or more markers placed in spatial relation to one or more vertebrae.

In certain embodiments, controlling the actuator to move the end-effector includes controlling the actuator to move the end-effector in a direction corresponding to a direction of application of the force and/or torque.

In certain embodiments, the end-effector is configured to move at a predetermined measured pace upon application and detection of user force and/or torque applied to the end-effector in excess of the predetermined minimum force and/or torque and the predetermined measured pace is a steady, slow velocity.

In certain embodiments, the robotic surgical system includes the neuromonitoring system for providing depth control and/or protection.

In certain embodiments, the surgical instrument is an osteotome.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIGS. 2A through 2D illustrate the principles of osteotomy;

FIG. 5A is an illustration of an example surgical instrument guide for use with a robotic surgical system;

FIG. 5B is an illustration of an example surgical instrument guide with an intermediate lock for use with a robotic surgical system;

Figure 1:
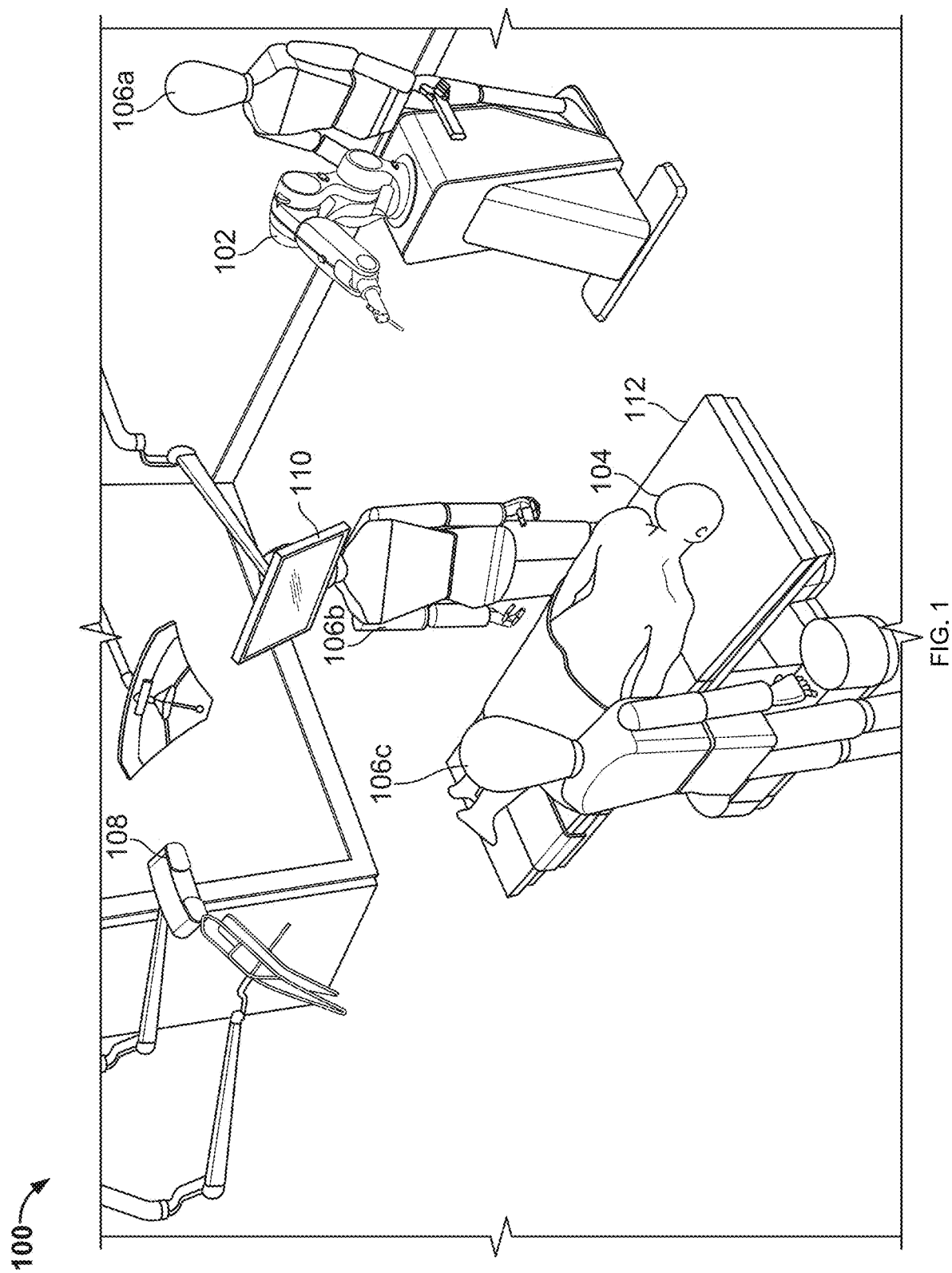
FIG. 1 is an illustration of an example robotic surgical system in an operating room.
Figure 3:
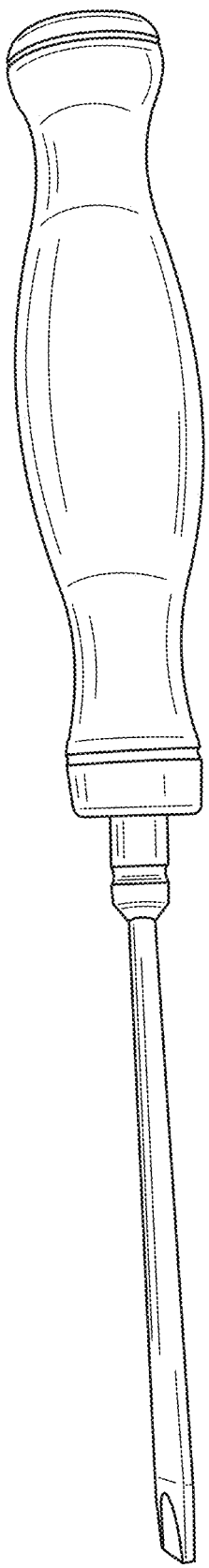
FIG. 3 is an illustration of an osteotome.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

FIG. 1 illustrates an example robotic surgical system in an operating room 100. In some implementations, one or more surgeons, surgical assistants, surgical technologists and/or other technicians (e.g., 106a-c) perform an operation on a patient 104 using a robotic-assisted surgical system. In the operating room 100 the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient 104. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion, neurosurgery, or orthopedic surgery. In some implementations, the surgical robotic system includes a surgical robot 102 on a mobile cart 114. The surgical robot 102 in the example shown in FIG. 1 is positioned in proximity to an operating table 112 without being attached to the operating table 112, thereby providing maximum operating area and mobility to surgeons around the operating table 112 and reducing clutter on the operating table 112. In alternative embodiments, the surgical robot 102 (or cart) is securable to the operating table 112. In certain embodiments, both the operating table 112 and the cart 114 are secured to a common base to prevent any movement of the cart or table 112 in relation to each other, even in the event of an earth tremor.

The mobile cart 114 may permit a user (operator) 106a, such as a technician, nurse, surgeon, or any other medical personnel in the operating room 100, to move the surgical robot 102 to different locations before, during, and/or after a surgical procedure. The mobile cart 104 enables the surgical robot 102 to be easily transported into and out of the operating room 100. For example, a user 106a may move the surgical robot 102 into the operating room 100 from a storage location. In some implementations, the mobile cart 114 may include wheels, a track system, such as a continuous track propulsion system, or other similar mobility systems for translocation of the cart. The mobile cart 114 may include an attached or embedded handle for locomotion of the mobile cart 114 by an operator (e.g., user 106a).

For safety reasons, the mobile cart 114 may be provided with a stabilization system that may be used during a surgical procedure performed with a surgical robot 102. The stabilization mechanism increases the global stiffness of the mobile cart 114 relative to the floor in order to ensure the accuracy of the surgical procedure. In some implementations, the wheels include a locking mechanism that prevents the cart 114 from moving. The stabilizing, braking, and/or locking mechanism may be activated when the machine is turned on. In some implementations, the mobile cart 114 includes multiple stabilizing, braking, and/or locking mechanisms. In some implementations, the stabilizing mechanism is electro-mechanical with electronic activation.

The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart 114. An actuator may move the robotic arm. The robotic arm may include a force control end-effector configured to hold a surgical tool. The robot 102 may be configured to control and/or allow positioning and/or movement of the end-effector with at least four degrees of freedom (e.g., six degrees of freedom, three translations and three rotations). The robotic surgical system can limit movement of a surgical instrument in a surgical instrument guide affixed to the end effector to movement along a trajectory, along a plane (or a portion of a plane) and/or to a particular depth.

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector 108 may be a camera, a video camera, an infrared detector, field generator and sensors for electromagnetic tracking or any other motion detecting apparatus. In some implementation, based on the patient and robot position, the display screen 110 displays a projected trajectory and/or a proposed trajectory for the robotic arm of robot 102 from its current location to a patient operation site. By continuously monitoring the patient 104 and robotic arm positions, using tracking detector 108, the surgical system can calculate updated trajectories and visually display these trajectories on display screen 110 to inform and guide surgeons and/or technicians in the operating room 100 using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae and/or other part of the patient 104 during the surgical procedure. An example robotic surgical system that may be used with the disclosed technology or modified for use with the disclosed technology is described in U.S. patent application Ser. No. 14/266,769, filed Apr. 30, 2014 and entitled Apparatus, Systems, and Methods for Precise Guidance of Surgical Tools, the contents of which are hereby incorporated by reference in their entirety.

Figure 4A:
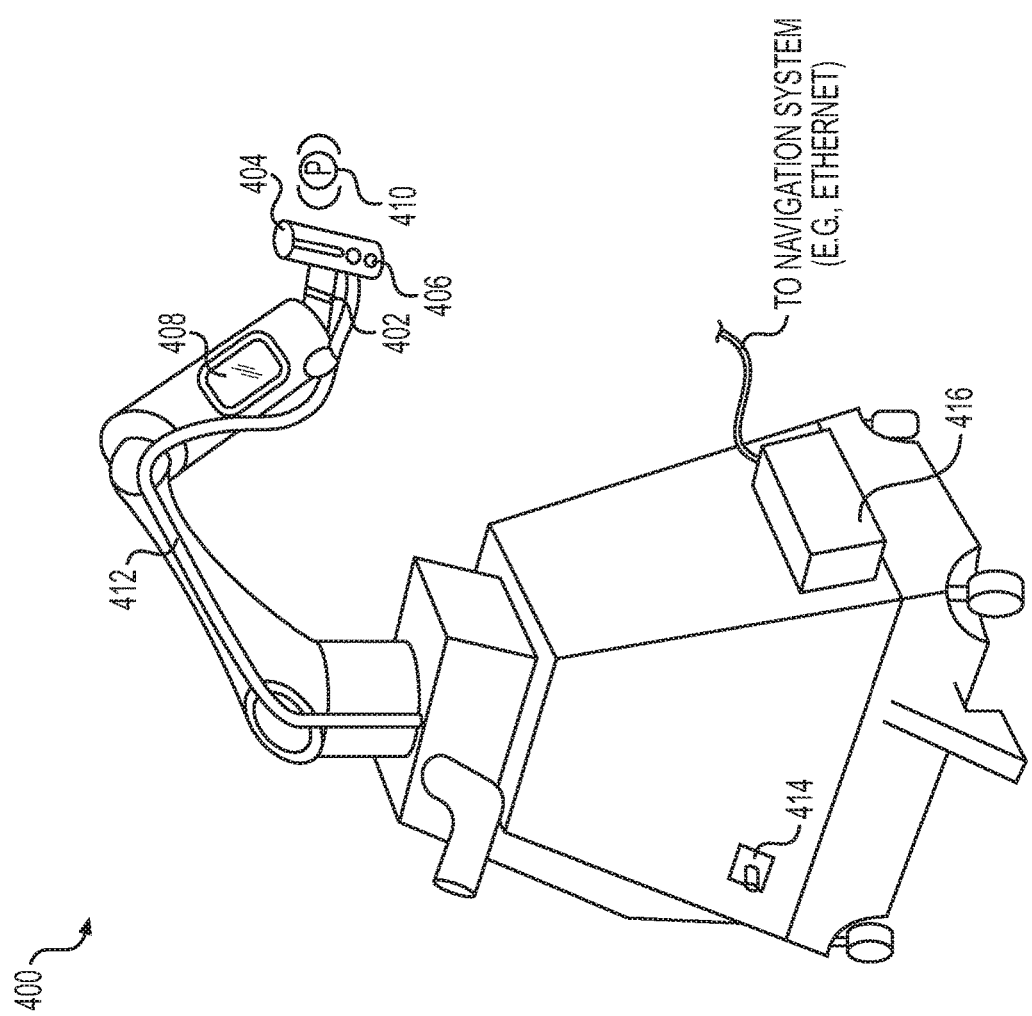
FIG. 4A is an illustration of an example robotic surgical system.

FIG. 4A is an illustration of an example robotic surgical system 400. Starting from the end effector 402, the robot holds an instrument guide 404. In certain embodiments, the instrument guide 404 is integrated with a depth block 410 that stops movement of the inserted instrument in a particular direction (e.g., max depth of penetration by the instrument can be set). Examples of surgical instrument guides that may be used herein or modified for use herein are disclosed in U.S. patent application Ser. No. 14/597,883, filed January 2015 and entitled "Notched Apparatus for Guidance of an Insertable Instrument Along an Axis During Surgery," the contents of which are hereby incorporated by reference in their entirety.

In certain embodiments, the guide 404 has sterilizable, reusable user interface 406. In certain embodiments, the interface 406 is an electrical assembly with one or more input devices for commanding the robotic surgical system 400. The one or more input devices may include two or more buttons configured to enable a user to place the robotic surgical system 400 in one of a rotation mode, a translation mode, or a combined translation and rotation mode. In some implementations, upon selection of a first button of the two or more buttons, the robotic surgical system 400 is in the rotation mode, upon selection of a second button of the two or more buttons, the robotic surgical system 400 is in the translation mode, and upon selection of both the first and second buttons, the robotic surgical system 400 is in the combined translation and rotation mode. In certain embodiments, this electrical assembly is provided for on or built into to the surgical instrument guide. In some implementations, the electrical assembly can be done separately (e.g., using overmolding on buttons and cable or epoxy resin to form an assembly which is integrated into the guide using a rapid locking device).

In some implementations, the surgical instrument guide 404 and input device(s) thereon (e.g., buttons) can be used for instructing the robotic system to translate along a line when the translation button is pressed, rotate around the line if the rotation button is pressed, and/or translate and rotate around the line if both buttons are pressed. The electrical assembly may be directly integrated into the surgical instrument guide 404.

The guide 404, in certain embodiments, is configured to be attached directly or indirectly to an end-effector 402 of the robotic surgical system 400. In some implementations, the robotic surgical system 400 is configured to allow robotically-assisted or unassisted positioning and/or movement of the end effector 402 by a user with at least six degrees of freedom. The six degrees of freedom may be three degrees of translations and three degrees of rotations.

In certain embodiments, a user interface 408 (e.g., for use by a surgeon) is on the robotic arm (e.g., the forearm). An example of such a user interface 408 is described in U.S. patent application Ser. No. 14/858,325, filed Sep. 18, 2015, entitled "Robot-Mounted User Interface for Interacting with Operation Room Equipment", the contents of which are hereby incorporated by reference in its entirety. It can based on the touch-screen technology and implemented using a tablet computer. This user interface 408 can be used to present the trajectory list to the user and allowing him/her to select one.

In certain embodiments, the robot 400 includes a neuromonitoring cable 412. The neuromonitoring cable 412 can pass through a hole (e.g., sealed) in the surgical instrument guide 404. A neuromonitoring probe can be incorporated with the guide 404 and/or surgical instrument, thereby allowing the robotic surgical system 400 to monitor a patient's neurological response to the procedure. In certain embodiments, a neuromonitoring interface 414 allows the robot 400 to communicate with an external neuromonitoring system. In other embodiments, the entire neuromonitoring system is external to the robotic surgical system 400 or the entire neuromonitoring system is integrated with the robotic surgical system 400.

Figure 4B:
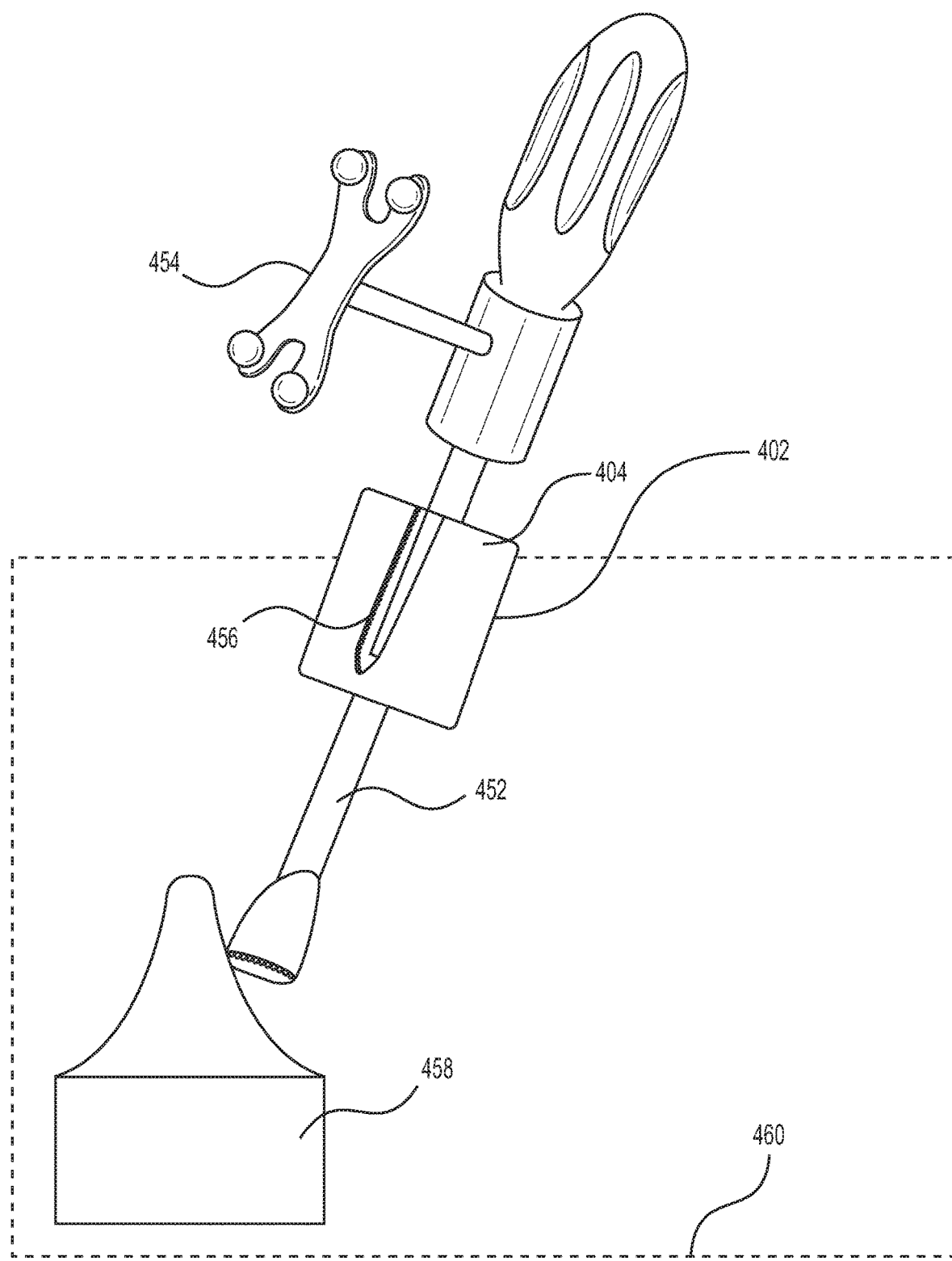
FIG. 4B is an illustration of as example integration of an osteotome instrument with a robotic surgical system.

FIG. 4B is an illustration of as example integration of an osteotome instrument 452 with a robotic surgical system. Other instruments (e.g., instruments for removing the cancellous bone, clean-up and closure, etc.) used in surgical procedures may similarly be integrated and/or used with the robotic surgical system 400. For example, the system may be used with Navlock™ Instruments by Medtronic of Minneapolis, Minnesota.

An osteotome 452 is rigid and sharp such that it can be used to remove hard, external parts of the bone 458, shown as a vertebrae in FIG. 4B. FIG. 4B illustrates a set-up for the use of the osteotome 452 with the robotic surgical system 400. The osteotome 452 is guided by the guide 404 which is held by the robot 400. In certain embodiments, the robot 400 moves only in the "locked" plane 460 (one of the two which create the wedge in the bone). In certain embodiments, the guide 404 allows (e.g., at the appropriate time) for translational movement of the osteotome 452 which is necessary to cut the bone (e.g., vertebrae). In certain embodiments, a user might use a hammer to advance the osteotome 452. In other embodiments, a user might advance the osteotome 452 using his hand.

A navigation marker 454 measures the position of the osteotome 452 which is necessary for the system to determine the locked planes (e.g., the planes along which the cuts to form the wedge in the bone are made). In an alternative set-up, the marker 454 can be on the robot 400 and robot's actual position (measured by robot's encoders and calculated using robot model) can be used to determine the position of the osteotome 452 in space.

In certain embodiments, the robot 400 prevents the osteotome 452 from getting too deep/beyond the tip of the desired wedge. This can be achieved be having the notch 456 in the guide 404 the correct distance above the patient—the navigation marker rod 454 would prevent the osteotome 452 from getting deeper than the notch 456 permits.

During an osteotomy procedure, in certain embodiments, the resection measurement is based on preoperative measurements. Determining the degree of the resection to accomplish the desired correction can be performed by the surgeon, by the computer system, or a combination thereof. For example, the system can determine the ideal shape of the spine, compare the ideal shape to a patient's spine, and determine the location of the resection and/or the amount that must be resected.

In certain embodiments, the tool holder 404 is integrated with neuromonitoring. In certain embodiments, depth control and protection is provided such that depth/insertion movement is stopped upon receipt of a trigger (e.g., external or internal). For example, in certain embodiments, neuromonitoring causes the robotic surgical system 400 to stop depth movement (e.g., in response to an external signal). The neuromonitoring system, in certain embodiments, includes the ability to react in response to a signal and/or generate a signal as well as the capability to stop the instrument (e.g., 452) and/or prevent the instrument (e.g., 452) from going beyond a certain threshold. In certain embodiments, the system 400 also moves the surgical instrument and/or surgical instrument guide 404 back (e.g., less depth of penetration in instances, for example, where a threshold has been exceeded) in response to a trigger. Neuromonitoring may be used in many surgical procedures, including osteotomy.

In certain embodiments, a neuromonitoring cable can pass through the sterile zone.

An example of how to pass a cable or electrical connection through the sterile zone is described in U.S. patent application Ser. No. 14/602,627, filed Jul. 27, 2015 and entitled "Sterile Drape and Adapter for Covering a Robotic Surgical Arm and Preventing Contamination of a Sterile Field," the contents of which are hereby incorporated by reference in their entirety. In certain embodiments, the neuromonitoring cable passes through the tool holder 404.

In certain embodiments, the robotic surgical system 400 integrates with a navigation system, such as StealthStation and Steathlink (e.g., to obtain trajectories from Stealthstation and for tracking real-time data)) by Medtronic of Minneapolis, Minnesota.

As shown in FIG. 5A, a guide 500, in some implementations, includes a tubular structure 506 (e.g., body), with a first longitudinal notch 522a along its length and a second longitudinal notch 522b along its length. In some implementations, the first notch 522a and second notch 522b are located on opposite sides/portions of the body 506 of the guide 500 as shown in FIG. 5A. In some implementations, the guide 500 includes two or more notches that are spaced evenly (as shown in FIG. 5A) or unevenly around the body of the guide.

In some implementations, the longitudinal notches 522a and 522b are slots. The longitudinal notches 522a-b, in some implementations, are sized in relation to one or more pegs that couples a navigation marker to a tool support. As the tool support slides through the guide 500, one of the notches 522a-b permits the tool support to slide along the axis defined by the guide while the guide is held in a fixed position by the robotic surgical system. The peg extends through one of the notches 522a-b and outside of the guide 500 and permits the navigation marker attached to the tool support via the peg to be viewed by a navigation camera along an entire range of movement of the tool support through the guide. In some implementations, the peg is utilized without the navigation marker to maintain the orientation of the surgical instrument. In some implementations, the navigation marker is used by navigation camera to track the surgical instrument. The notches 522a-b may constrain movement of the marker in a fixed orientation along the axis defined by the guide. In some implementations, longitudinal notches 522a-b are sized in relation to a peg to permit the surgical instrument to slide along the axis of insertion in reference to the tool support.

Among other things, incorporation of two or more notches, such as notches 522a and 522b, permits for ambidextrous manipulation of the end effector and/or tool. Moreover, it permits positioning of the robotic surgical system on both sides of the operating room table.

Furthermore, it permits positioning of the robotic surgical system on both sides of the operating room table in reference to a navigation system (e.g., tracking camera).

In some implementations, the guide 500 includes one or more input devices, such as electro-mechanical buttons. For example, the guide 50 may include two electromechanical buttons 508a and 508b. In some implementations, the guide 50 includes an activation switch 560. The activation switch 560 may be separate from the buttons 508a and 508b. The activation switch 560 may be a presence detection that can be used for enabling movements of the surgical robot. The types of movements may be defined by the buttons 508a and/or 508b. The present detection may include a long button that is pressed when a user grabs the handle (e.g., to thereby move the handle). In some implementations, the activation switch detects the presence of a hand on the handle.

In some implementations, a user may use the one or more input devices to select to enter a translation mode, positioning mode, axis rotation mode, axis insertion mode and/or axis position mode. In some implementations, the guide 500 includes an enabling button, rotation button and/or a translation button. In some implementations, the enabling button must be selected with one or more other buttons to enable movement of the end effector. For example, to rotate the end effector, the user may need to select the enabling button and the rotation button. Similarly, to enable translations of the end effector, the user may need to select the enabling button and the translations button. In some implementations, the end effector may enter a course positioning mode when a user selects the enabling button, translations button, or rotations button. In some implementations, selection of the enabling button causes the robotic arm to enter the positioning mode in which the user is able to position the tool appropriately and allows the operator to freely move the robotic arm (e.g., via course movements).

Selection of the translation mode allows, in some implementations, the end effector to be moved along a plane (e.g., a plan in line with the end of a tool such as a drill guide). An operator may use the translation mode to make fine movements with the end effector and to find an entry point. Selection of the rotation mode locks movement of the end effector except rotations (e.g., the manipulator may only be rotated). In some implementations, activation of the rotation mode permits an operator to make fine rotations around an entry point. In axis rotation mode an operator may rotate the end effector around a specific axis (e.g., the axis formed by a drill guide). In axis position mode, an operator may move the end effector without changing an axis (e.g., the axis formed by a drill guide). In axis insertion mode, an operator may move the end effector along a trajectory.

The various positioning modes allow an operator to quickly and accurately move the end effector to a desired position (e.g., on or along a determined trajectory). When all of the buttons are released, in some implementations, the robot actively holds the position of the end effector. For example, if a drill guide is coupled to the end effector, an operator may insert a drill into the drill guide without moving the position of the end effector or drill guide. Thus, after carefully positioning the drill guide along a desired trajectory, an operator may accurately drill along the desired trajectory.

FIG. 5B is an illustration of an example surgical instrument guide 530 with an intermediate lock 532 to lock the position of the surgical instrument in the guiding tube 506. Instead of having a long guiding tube, the robot may move the guiding tube 506 along a trajectory (e.g., in a straight line) thus creating a very long "virtual" guidance without compromising haptic feedback for the surgeon. Additionally, the intermediate lock 532 enables the surgical instrument to be placed in the guiding tube prior to determining the correct trajectory. After the correct trajectory is determined, the robotic arm may be moved away from the patient such that, for example, the vertebrae may be accessed by a surgeon.

After the vertebrae is prepared, the robot can assist the surgeon in finding the right trajectory again, thus significantly decreasing the time necessary for screw placement in comparison to manual spinal surgeries.

An intermediate lock 532 may be placed at an initial distance 534, such as 80 mm, from an entry of the guiding tube 506. In some implementations, the initial distance is 80 mm. In some implementations, the initial distance is between 70-90 mm, 60-80 mm, or 80-100 mm. In some implementations, the initial distance corresponds to the length of the longest pedicle screws used with a small amount of margin (e.g., 5, 5, 15, or 20 mm of margin). In some implementations, the intermediate lock 532 is a unidirectional lock that only blocks insertion movement. In some implementations, the initial distance 534 is long enough to allow guidance of the inserted instrument when intermediate lock 532 is in the locked position. For example, the initial distance, in some implementations, is 30 mm. In some implementations, the initial distance is between 25-25 mm, 20-40 mm, or 35-50 mm. In some implementations, the intermediate lock 532 is a bidirectional lock that blocks insertion and removal of the surgical instrument.

When the intermediate lock 532 is released (e.g., unlocked), the surgical instrument may be slide further into the guide. In some implementations, the insertion distance 536 (e.g., distance the surgical instrument can move forward after the intermediate lock 532 is released) is selected to allow sufficient guidance of the surgical instrument inside the vertebrae. In some implementations, the insertion distance is 80 mm. In some implementations, the insertion distance is between 70-90 mm, 60-80 mm, or 80-100 mm. This may be defined by the type of surgery and may be, for example, the length of a pedicle screw with some margin (e.g., 40-80 mm of total travel; e.g., 55, 60, 65, 70, or 75 mm total). The intermediate lock 532 may be implemented using a variety of mechanisms. The intermediate lock 532 may be a spring lock (e.g., a button that is pressed through a hole on the guide by a spring when the instrument is slide into a particular position). The intermediate lock 532 may be a small device that blocks the movement of the tool inside the guide 506. For example, the intermediate lock 532 may block the peg that holds a marker to a tool support. The intermediate lock 532 may be one or two bars that prevent movement of the instrument unilaterally or bilaterally, respectively. For example, two bars may be used to prevent the peg from moving. In some implementations, a lock is provided to lock the surgical instrument in place when it is fully inserted in the guide 506. The lock may be designed and/or function similarly to the intermediate lock.

Figure 5C:
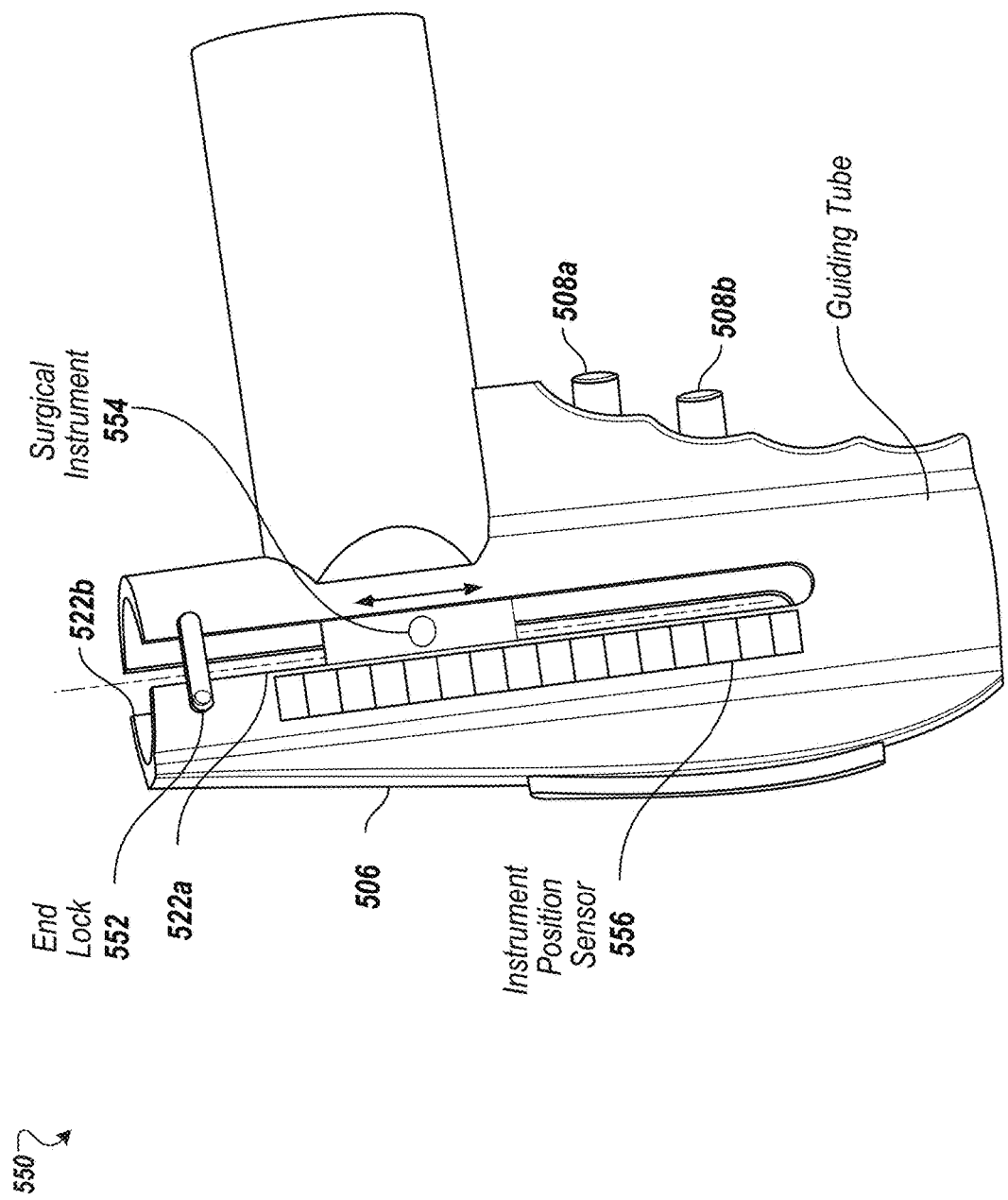
FIG. 5C is an illustration of an example surgical instrument guide with an end lock for use with a robotic surgical system.

FIG. 5C is an illustration of an example surgical instrument guide 1150 with an end lock 552 to lock the position of the surgical instrument in the guiding tube 506. The end lock may be used to prevent the surgical instrument from accidentally being removed from the guiding tube 506. In some implementations, an instrument position sensor 556 (e.g., position detector) is integrated in the guiding tube 506 (e.g., any guiding tube described herein). The instrument position sensor 556 may be an inductive sensor, capacitive sensor, resistive sensor, mechanical end switches, optical measuring device, force sensing device, or other similar position sensor. When the surgical instrument is inside the tube 506, the relative position of the instrument may be measured by the instrument position sensor 556. In some implementations, the sensor 556 detects discrete positions of the instrument inside the guiding tube 506. For example, the sensor 556 may detect when the surgical instrument is at a top, bottom, or middle position within the guide.

In some implementations, the robot generates movement of the tube 506 in response to the position of the instrument (e.g., to achieve movement along a desired trajectory). The movement may be generated only when the surgical instrument is at the extremities of the tube 506 (e.g., at either end of the notch 522). The combination of these features and the ability to combine movement of the instrument inside the guiding tube 506 and guidance of the tube 506 by the robot to provides the ability to obtain long and complicated trajectories using simple and short surgical instrument guide tubes (e.g., 506) held by the robot.

The end lock 552 may be a spring lock (e.g., a button that is pressed through a hole on the guide by a spring when the instrument is slide into a particular position). The end lock 552 may be a small device that blocks the movement of the tool inside the guide 506. For example, the end lock 552 may block the peg that holds a marker to a tool support. The end lock 552 may be one or two bars that prevent movement of the instrument unilaterally or bilaterally, respectively. For example, two bars may be used to prevent the peg from moving.

Figure 6:
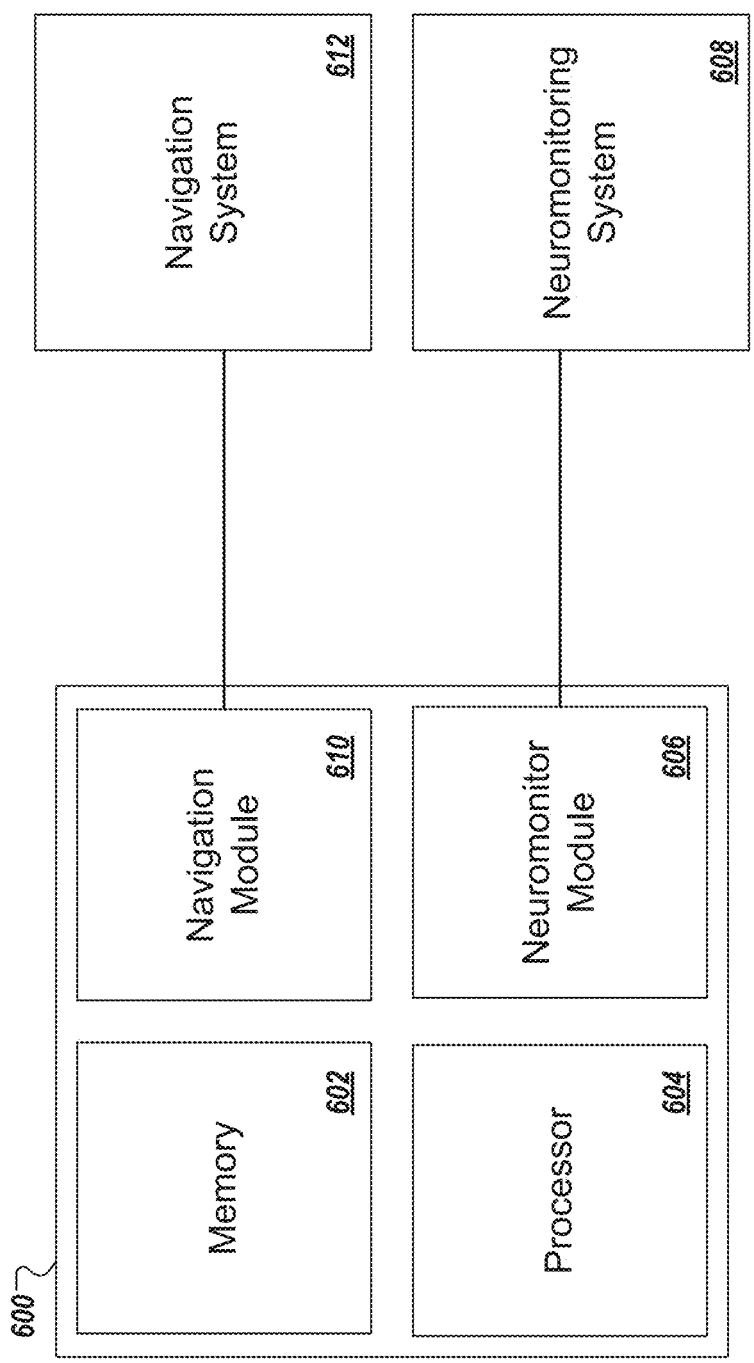
FIG. 6 is a diagram of a robotic surgical system for use in a surgical procedure performed on a patient.

FIG. 6 is a diagram of a robotic surgical system 600 for use in a surgical procedure performed on a patient. In this example, the system 600 includes a robotic arm having an end-effector thereon and an actuator for controlled movement of the robotic arm and positioning of the end effector. A processor 604 and memory 602 are used to control movement of the robotic arm and coordinate behavior of the system 600 with various modules. As described above, this allows the system 600 to control the trajectory and/or insertion depth of a surgical instrument in a guide affixed to the end effector. In certain embodiments, the system 600 includes a neuromonitoring module 606 for implementing real-time neuromonitoring during the surgical procedure. In certain embodiments, the neuromonitoring module 606 receives a trigger based on a neurological response of a portion of a nerve structure of the patient that is measured by a neuromonitoring system 608. The neuromonitoring module 606, upon receipt of the trigger, prevents deeper insertion into the patient of a surgical instrument guided by the robotic surgical system 600. Preventing deeper insertion into the patient of a surgical instrument can be accomplished by moving, by the robotic surgical system 600, a position of the end-effector away from the patient (e.g., along an axis—such as the trajectory of an instrument held by the end-effector). A neuromonitoring cable can be used by the neuromonitoring system 608 to detect a neurological response that results in the neuromonitoring system 608 sending the trigger to the neuromonitor module 606. In certain embodiments, the surgical instrument guide is arranged to pass a neuromonitoring cable therethrough. In certain embodiments, the surgical instrument guide is integrated with the neuromonitoring system 608 such that a neuromonitoring cable can pass through the guide and thus through a sterile zone.

In certain embodiments, the neuromonitoring system 608 is separate from the robotic surgical system. In other embodiments, the neuromonitoring system 608 is part of the robot 600.

In certain embodiments, the robot 600 includes a navigation module 610 that communicates with a navigation system 612 that can monitor the position of the patient (e.g., the patient's skeletal structure, such as a specific piece or area of a bone), the robot, and/or surgical instrument. For example, the position of the surgical instrument can be determined by a navigation system 612 based at least in part on the position of a marker on the surgical instrument. In another example, the position of the surgical instrument is determined by a navigation system 612 based at least in part on the position of a marker on the robotic surgical system 600 and the robotic arms actual position (e.g., as measured by the robotic surgical systems 600 encoders and calculated using the robotic surgical systems 200 movement model).

Figure 7:
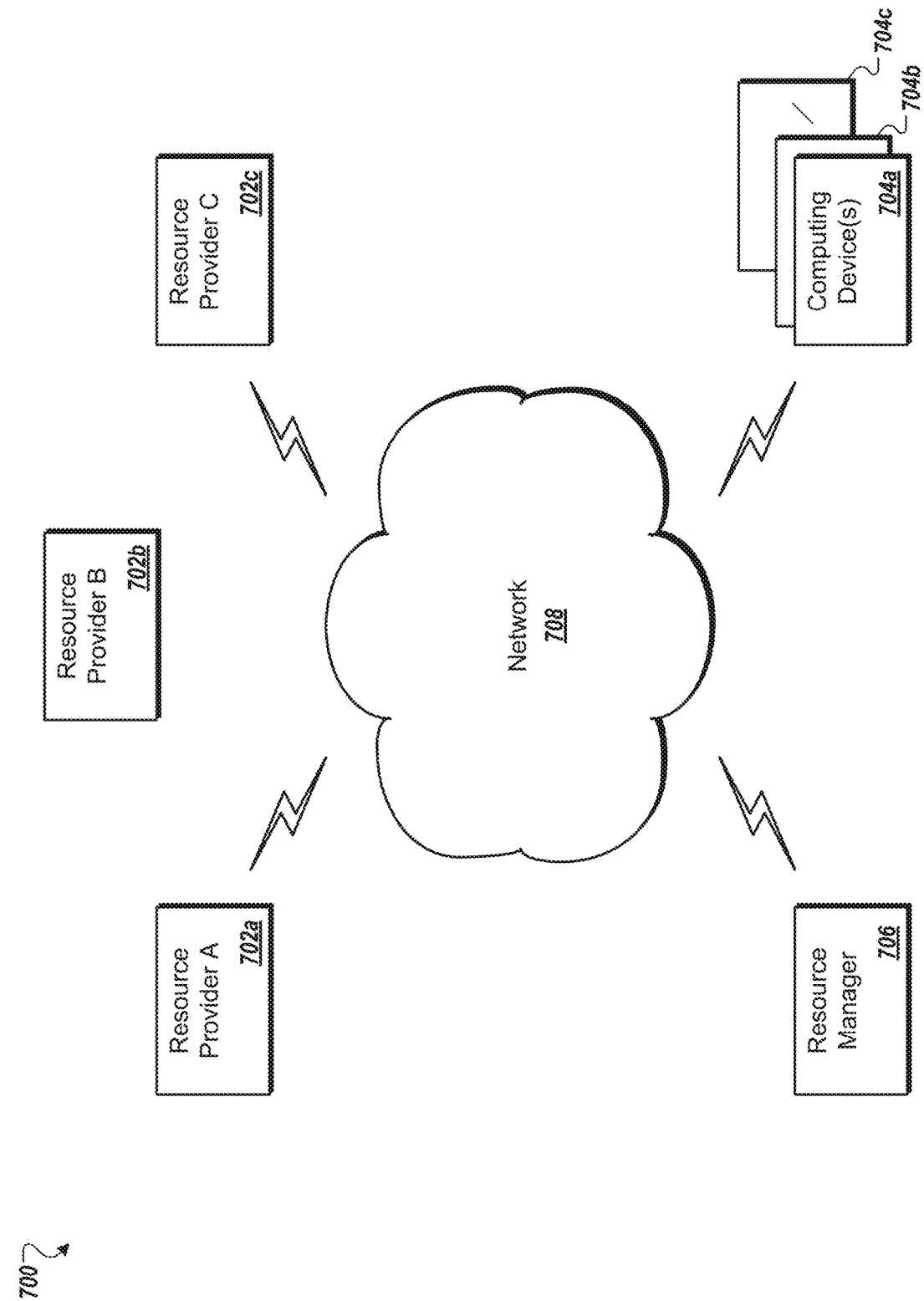
FIG. 7 shows a block diagram of an exemplary cloud computing environment.

As shown in FIG. 7, an implementation of a network environment 700 for use in the robotic surgical system is shown and described. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
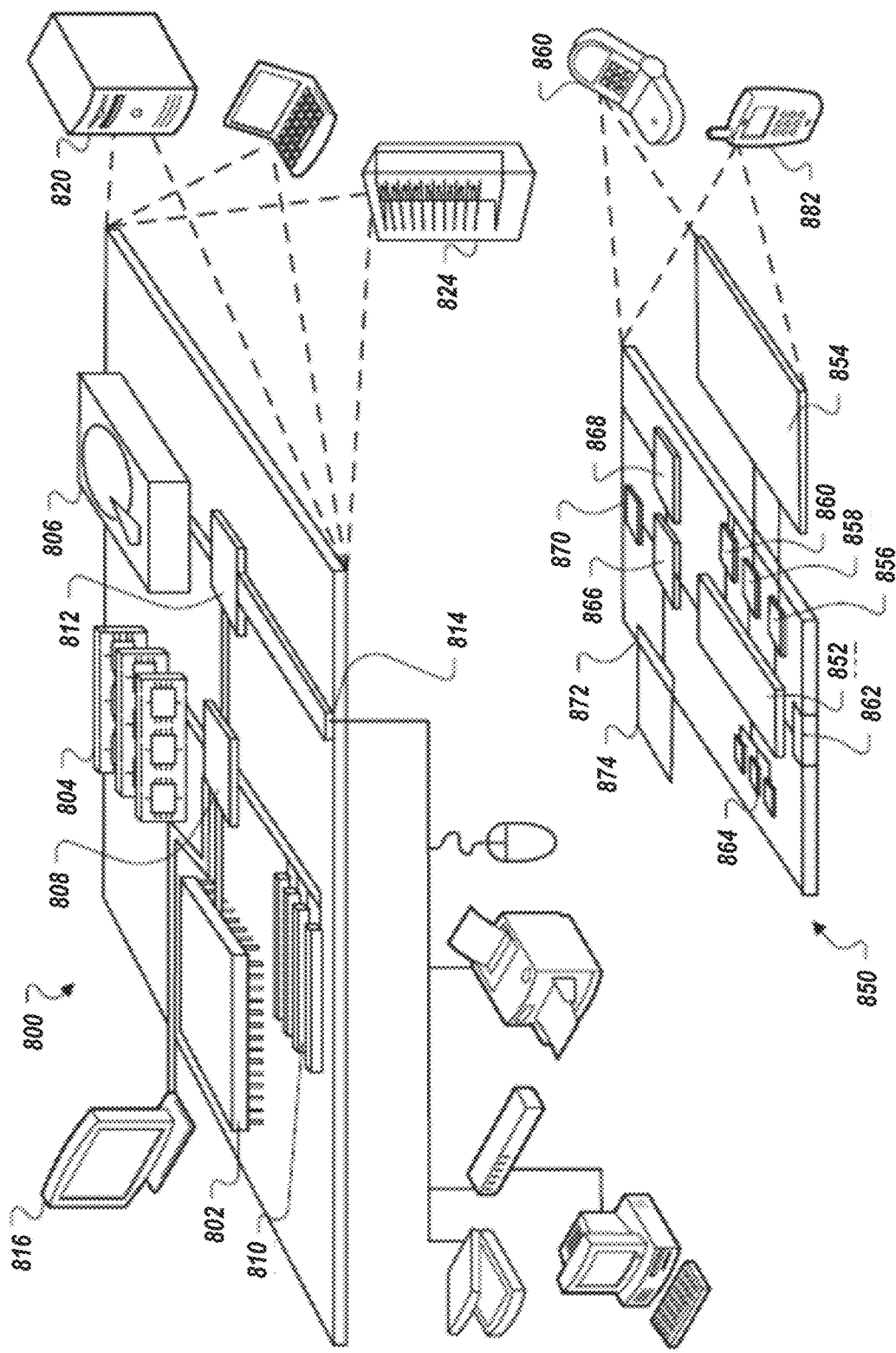
FIG. 8 is a block diagram of a computing device and a mobile computing device.

FIG. 8 shows an example of a computing device 800 and a mobile computing device 850 that can be used to implement the techniques described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provided as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for use in performing a surgical procedure with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed:

1. A method of controlling the position of an end-effector of a robotic surgical system, the method comprising:
   receiving a surgical instrument in a surgical instrument guide affixed to the end effector;
   receiving, by a neuromonitoring module of the robotic surgical system, a trigger from a neuromonitoring system, wherein the robotic surgical system includes:
     a robotic arm having the end-effector connected thereto,
     an actuator that controls movement of the robotic arm and positioning of the end effector, thereby controlling the trajectory and insertion depth of the surgical instrument received in the surgical instrument guide affixed to the end effector, and
     the neuromonitoring module for real-time neuromonitoring during a surgical procedure while the surgical instrument is positioned in the surgical instrument guide; and controlling, by a processor of a computing device in the robotic surgical system, a position of the end-effector to prevent deeper insertion into a patient of the surgical instrument guided by the robotic surgical system upon receipt of the trigger, wherein the surgical instrument guide is integrated with the neuromonitoring module.

2. The method of claim 1, wherein preventing deeper insertion into the patient of the surgical instrument includes moving, by the robotic surgical system, a position of the end-effector away from the patient.

3. The method of claim 1, wherein the surgical instrument guide of the end effector is arranged to pass a neuromonitoring cable therethrough.

4. The method of claim 1, wherein the surgical instrument guide is integrated with the neuromonitoring system such that a neuromonitoring cable can pass through a sterile zone.

5. The method of claim 1, wherein the neuromonitoring system is a separate system which is not integrated with the robotic surgical system.

6. The method of claim 1, wherein the neuromonitoring system comprises a cable that extends through the surgical instrument guide connected to the end-effector.

7. The method of claim 1, wherein the surgical instrument guide comprises a user interface thereon.

8. The method of claim 1, wherein the surgical instrument guide comprises a user interface thereon and includes one or more buttons.

9. The method of claim 1, wherein the surgical instrument guide comprises a block or notch for preventing further insertion of the surgical instrument.

10. The method of claim 1, further comprising:
receiving, by a navigation module in the robotic surgical system, a navigation signal indicating movement of a navigation marker; and
moving, by the robotic surgical system, the end-effector based on the navigation signal.

11. The method of claim 1, wherein the robotic surgical system comprises a touch screen user interface on the robotic arm of the robotic surgical system.

12. A method of cutting a bone of a patient along a plane, the method comprising:
moving, by the robotic surgical system, an end effector to a trajectory, wherein the robotic surgical system includes:
a robotic arm having the end-effector connected thereto; and
an actuator that controls movement of the robotic arm and positioning of the end effector, thereby controlling the trajectory of a surgical instrument received in a surgical instrument guide connected to the end effector;

receiving the surgical instrument in the surgical instrument guide connected to the end effector;

maintaining the position of the end-effector in a locked plane in which the surgical instrument received in the surgical instrument guide is only allowed to move within a single plane defined by the locked plane, wherein the surgical instrument is a bone cutting tool;

receiving, by a neuromonitoring module of the robotic surgical system, a trigger from a neuromonitoring system;

preventing, by a processor of a computing device in the robotic surgical system, a deeper insertion into a patient of the surgical instrument guided by the robotic surgical system upon receipt of the trigger, wherein the surgical instrument guide is integrated with the neuromonitoring module.

13. The method of claim 12, wherein:
surgical instrument guide supports an osteotome as the bone cutting tool; and
the locked plane is a single plane that defines one of the two which create a wedge in the bone to be cut.

14. The method of claim 12, further comprising determining the locked plane based at least in part on the position of a navigation marker on the surgical instrument, the marker being tracked by a navigation system in communication with the robotic surgical system.

15. The method of claim 12, permitting, by the robotic surgical system, manual movement of the end-effector to a position for an operation.

16. The method of claim 12, wherein the robotic surgical system is adapted to allow robotically assisted or unassisted positioning and movement of the end-effector by a user with at least six degrees of freedom, wherein the six degrees of freedom include three degrees of translation and three degrees of rotation.

17. The method of claim 12, further comprising moving, by the robotic surgical system, the end-effector at a predetermined measured pace upon application and detection of user force applied to the end-effector in excess of a predetermined minimum force and the predetermined measured pace is a steady velocity.

18. The method of claim 12, wherein preventing deeper insertion into the patient of the surgical instrument includes moving, by the robotic surgical system, a position of the end-effector away from the patient.

19. The method of claim 12, wherein the surgical instrument guide of the end effector is arranged to pass a neuromonitoring cable therethrough.

* * * * *